(12) United States Patent
Garbez et al.

(10) Patent No.: US 8,702,646 B2
(45) Date of Patent: Apr. 22, 2014

(54) SUBMERSIBLE VALVE FOR A BREAST MILK COLLECTION DEVICE WITH SELF CONTAINED RESERVOIR

(76) Inventors: Dan Garbez, Sacramento, CA (US); Stella Dao, Sacramento, CA (US); Dave Paul, Scotts Valley, CA (US); Ben Sutton, Scotts Valley, CA (US)

(*) Notice: Subject to any disclaimer, the term of this patent is extended or adjusted under 35 U.S.C. 154(b) by 0 days.

(21) Appl. No.: 13/585,250

(22) Filed: Aug. 14, 2012

(65) Prior Publication Data
US 2014/0052056 A1 Feb. 20, 2014

(51) Int. Cl.
*A61M 1/06* (2006.01)
(52) U.S. Cl.
USPC ............................................................ 604/74

(58) Field of Classification Search
USPC ...................................................... 604/74–76
See application file for complete search history.

(56) References Cited

U.S. PATENT DOCUMENTS 7,559,915 B2 * 7/2009 Dao et al. ........................ 604/74
8,118,772 B2 2/2012 Dao

* cited by examiner

*Primary Examiner* — Nicholas Lucchesi
*Assistant Examiner* — Leah Stohr
(74) *Attorney, Agent, or Firm* — Howard B. Rockman; Mercedes V. O'Connor

(57) ABSTRACT

The present invention is an improved valve system for a naturally shaped and hands-free human breast milk collection device that fits into a mother's existing nursing or standard brassiere. The invention comprises a submersible valve system within a breast milk collection device, which can significantly increase the breast milk collection capacity of the device without increasing the overall size of the device.

3 Claims, 4 Drawing Sheets

SUBMERSIBLE VALVE FOR A BREAST MILK COLLECTION DEVICE WITH SELF CONTAINED RESERVOIR

This invention relates to the field of human breast milk collection devices and more specifically, to breast milk collection devices which can fit discreetly within a woman's brassiere to provide hands-free breast milk collection, and can significantly increase breast milk collection capacity within the collection device without increasing the size of the collection device.

BACKGROUND OF THE INVENTION

Breast pumps are well known, but the field of breast pump devices with self-contained breast milk reservoirs which can be used discreetly by fitting them within a woman's brassiere, often under ordinary clothing so that a woman can use a breast pump around others discreetly, is relatively new. The only known devices in this field, upon which this invention improves, are taught in U.S. Pat. Nos. 7,559,915 and 8,118,772 (Dao, Garbez), the disclosures of which patents are incorporated by reference herein.

To provide adequate milk collection capacity for lactating women using a breast pump, presently available breast milk reservoir devices are large, and when placed in a brassiere give a lactating woman an enhanced appearance. These breast milk collection devices are frequently used by a lactating woman underneath her clothing and in the presence of others. An embodiment of these devices utilizes a flap valve between the vacuum source and the stored milk, and the devices reach their maximum collection capacity once the collected milk in the reservoir reaches the bottom of the flap valve.

The risk from overfilling above the level of the flap valve is that when the pump is turned off, the valve may not prevent the backflow of milk into the breast funnel. This constraint leaves possibly more than half the potential volume of the reservoir unused.

Therefore, a need exists for an improved valving system which can allow milk extracted from the breast to flow into the reservoir and continue to be securely stored there even after the pump is turned off and the valving system is submersed in the collected milk, by preventing milk from returning into the breast funnel from the reservoir even in the absence of negative pressure holding the valve closed. This valve system would facilitate much larger milk collection volumes than the existing valve systems within the same size devices, and facilitate embodiments of the devices which are smaller and even more discreet for lactating women with low milk output and minimal collection requirements.

SUMMARY OF THE INVENTION

The present invention is an improved valve system for a compact and hands-free human breast milk collection device that fits into a mother's existing nursing or standard brassiere. The device which contains this improved valve system can be attached to a conventional electric or manual vacuum pump for milk collection. The invention comprises a valve system which, in an embodiment, is at the distal end of a breast adaptor which has a funnel-shaped inlet coupled to a reservoir, wherein when the breast is inserted into the breast adaptor, the breast milk is expressed into the reservoir through a unique valve system and the milk is stored in the reservoir until the device is removed and the collected milk emptied into a container. In an embodiment, the valve system is integral to or mounted concentrically on a second end of the breast adaptor, is adapted to be connected to an external suction source, and has an integral or detachable flexible membrane which allows the passage of milk into the reservoir, while preventing the collected milk in the reservoir to flow back into the breast adaptor.

The valve system alternately opens and closes communication between the breast adaptor and the reservoir, allowing milk extracted from the breast to pass through the funnel and valve system into the reservoir. The valve system continues to function normally as the level of milk within the reservoir rises and submerses the valve's one-way apparatus, allowing most of the volume of the reservoir to be utilized.

In an embodiment, the flexible membrane is a duckbill valve, whose outer walls, when submersed, are compressed by the fluid pressure of the milk collected in the reservoir, closing the valve and preventing the backflow of milk into the breast adaptor even in the absence of negative pressure from the pump. When vacuum pressure is applied to the valve, the vacuum pressure pulls the interior walls of the duckbill valve together by exerting negative pressure on the valve interior wall surfaces, which closes the valve. When the pump is in the positive pressure range of its cycle, the valve opens, allowing milk to flow into the collection container, and then the valve closes again during the negative pressure range of the cycle, or after pumping when it is turned off or disconnected. As the pump's cycle alternates from negative to positive or ambient pressure, the fluid pressure on the duckbill valve from the milk in the reservoir keeps the valve closed until positive pressure advances the milk from the drip tube and the valve assembly, forcing the duckbill valve into an open position, and the milk flows into the reservoir.

BRIEF DESCRIPTION OF THE DRAWINGS

The invention will be more fully understood by reference to the following drawings which are for illustrative purposes only.

DETAILED DESCRIPTION OF THE ILLUSTRATED EMBODIMENT

The breast milk collection device with a self contained reservoir, as described herein and in U.S. Pat. Nos. 7,559,915 and 8,188,772 (incorporated by reference herein) significantly improves a lactating woman's ability to express and pump breast milk by providing a device that can be used by the lactating woman at a stationary place, such as while at work, in a vehicle with a power adaptor, or other public and private places with a minimum of interference or immodesty, and relative minor disruption to the lactating woman's normal activities. In addition, the present invention can function as a passive breast milk collection reservoir when a breast pump is not connected to the reservoir device.

The inventive one-way valve structure of the present invention is submersible in the collected breast milk in the reservoir, and functions to allow breast milk to enter the reservoir from a drip tube and valve assembly connected to the cyclic application and relief of vacuum pressure to the drip tube during a cessation or relief of the vacuum pressure application cycle, while at the same time preventing the milk from entering the drip tube or vacuum source from the reservoir during the vacuum pressure application portion of the cycle.

Figure 1:
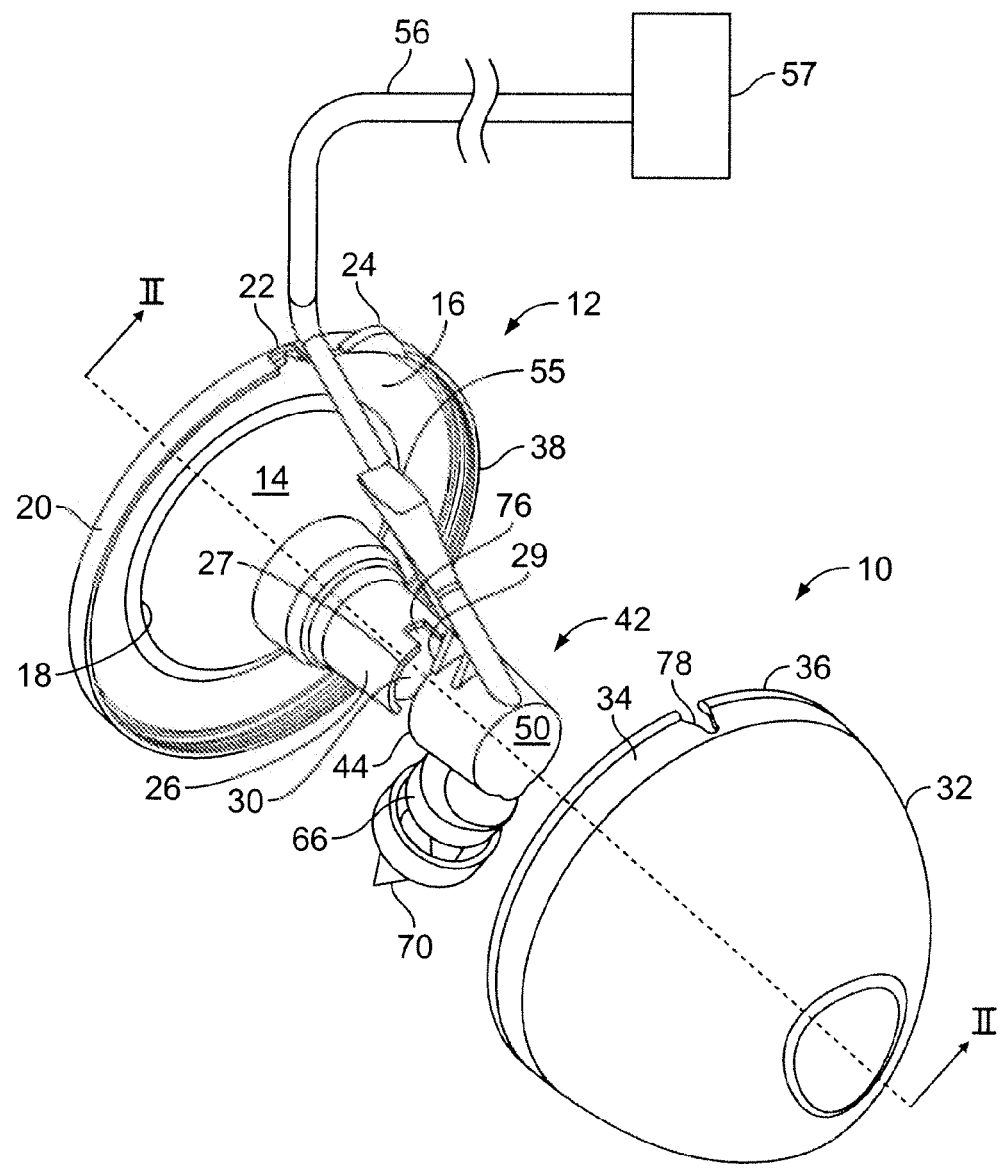
FIG. 1 is an exploded perspective view of the breast milk collection device with self-contained reservoir of the present invention, illustrating the submersible valve disposed below the drip tube.
Figure 2:
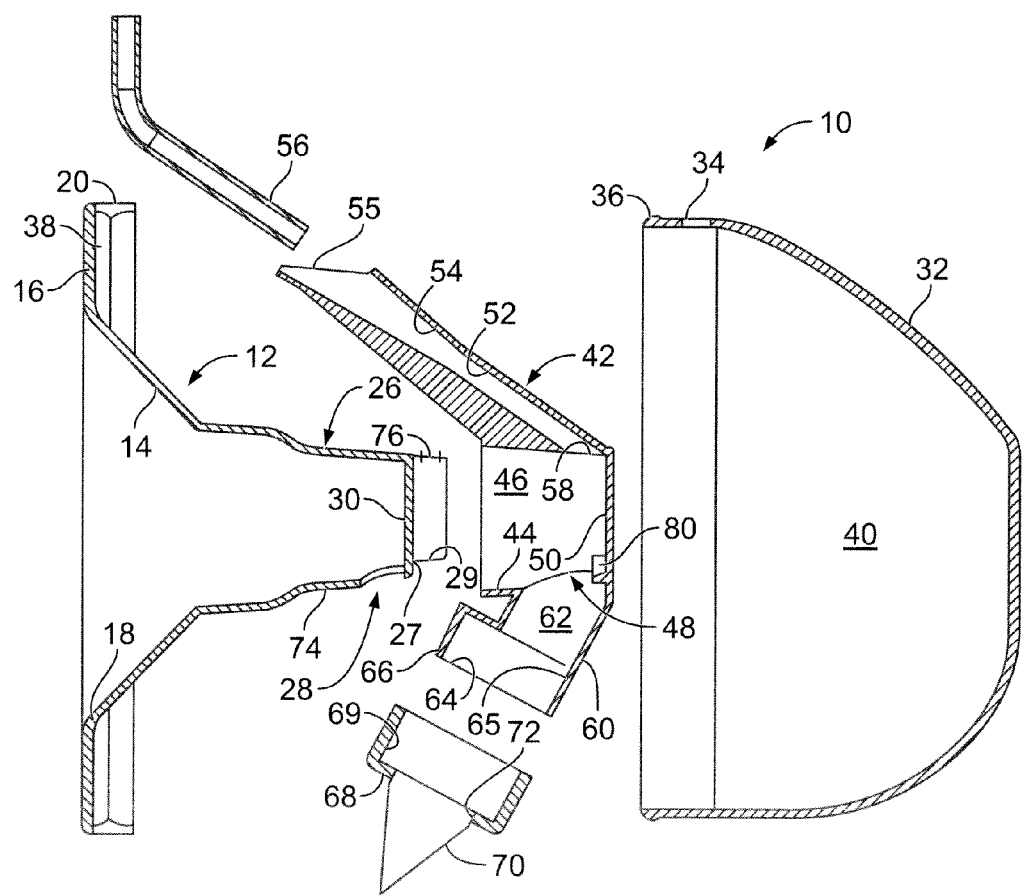
FIG. 2 is an exploded cross-section elevation view of the beast milk collection device of FIG. 1, taken along line II-II of FIG. 1.

Referring to FIGS. 1 and 2, the breast milk collection device 10 of the present invention includes an adaptor 12 having a funnel-shaped central portion 14 within which a lactating woman's breast is to be inserted, and a wall or plate 16 circumscribing the wide end 18 of the adaptor 12. Plate 16 includes an outer rim 20 extending inwardly from the outer edge of plate 16. Outer rim 20 includes an opening 22 and a tab 24 for purposes to be explained. The funnel-shape of portion 14 of adaptor 12 is selected and can be adapted to accommodate a wide variety of female breast shapes and sizes.

The funnel shaped portion 14 of adaptor 12 progressively narrows and terminates at a hollow drip tube 26 having an aperture 28 adjacent the distal end 30 of drip tube 26. A shroud portion 27 extends partially around and beyond distal end 30, forming a chamber 29. In the illustrated embodiment, drip tube 26 is made of a material that prevents the drip tube from collapsing when vacuum pressure is applied to the drip tube.

Figure 3:
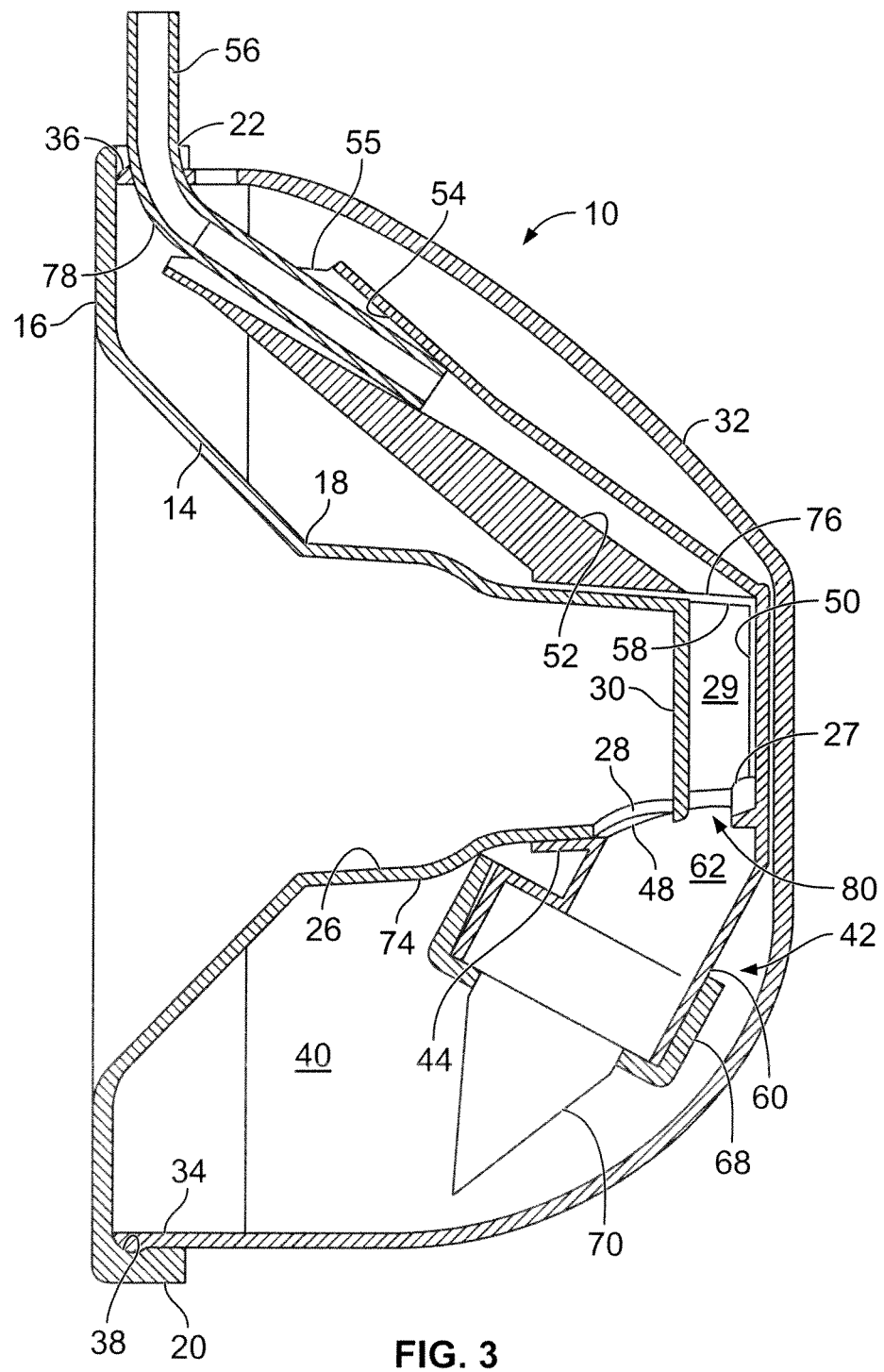
FIG. 3 is a cross-section elevation assembly view of the breast milk collection device of FIG. 1, illustrating the vacuum hose attached to the vacuum inlet channel of the device.
Figure 4:
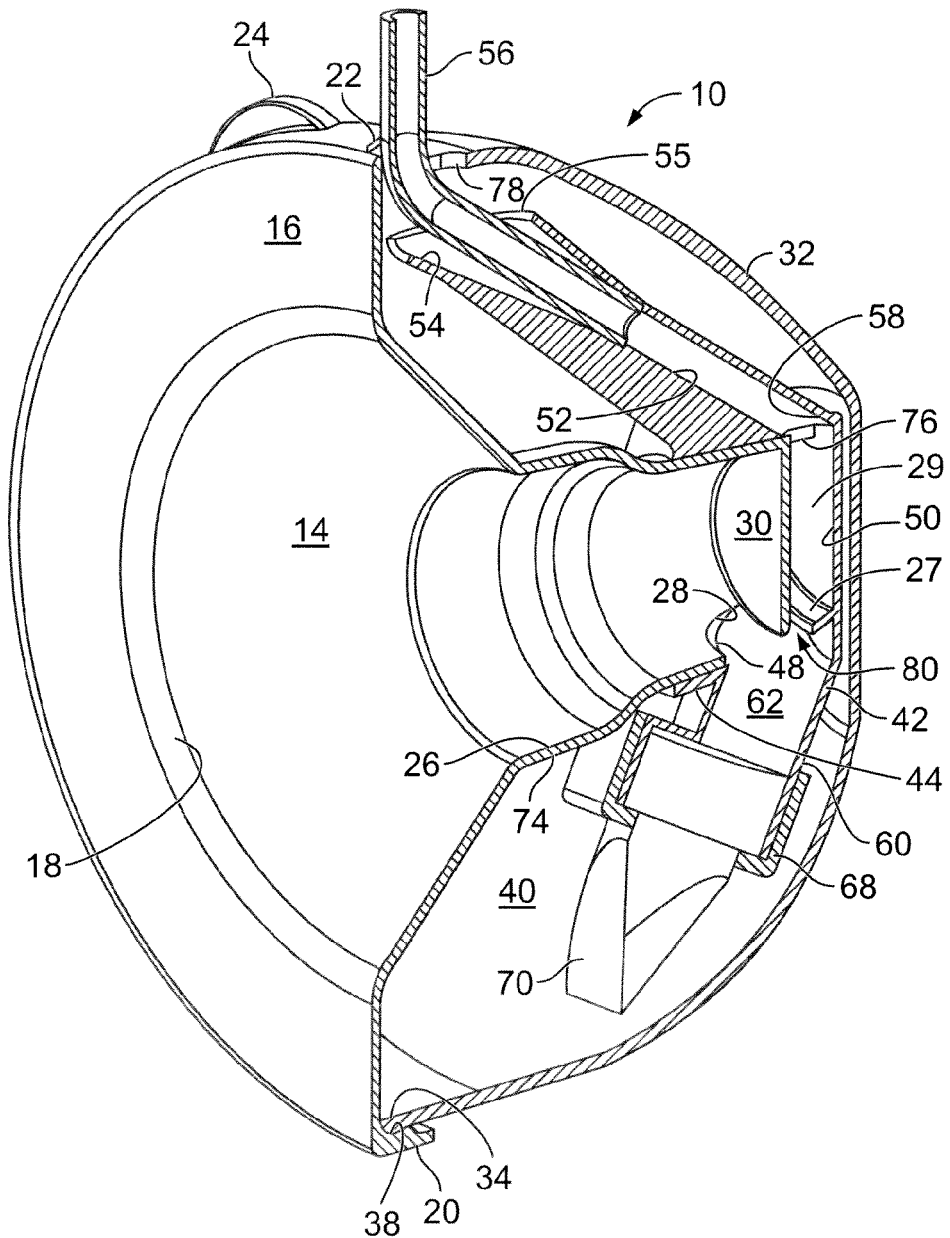
FIG. 4 is a perspective cross-section assembly view of the breast milk collection device shown in FIG. 1.

Drip tube 26 receives milk expressed from the lactating woman's breast during the pumping operation, to be explained. A reservoir 32 has a rim 34 including a radially outward extending bead 36 that removably engages circular groove 38 in outer rim 20 of adaptor 12, providing a snap-fit removable connection between reservoir 32 and adaptor 12, as shown in FIGS. 3 and 4. Breast milk flowing through funnel shaped adaptor 12 also flows to drip tube 26, and through aperture 28 and eventually into the internal volume 40 of reservoir 32, where the breast milk fills the reservoir 32. The drip tube 26 and funnel shaped adaptor 12 protrude a distance into the confines of the reservoir's internal volume, which can be an inch or more, giving the nipple of the breast room to elongate in a forward motion during pumping, providing an optimal nipple orientation for milk expression. The compact shape of the reservoir 32 allows the entire device 10 to fit discretely within a woman's standard or nursing brassiere. The adaptor 12 and reservoir 32 comprise a single self-contained unit that does not depend on external milk collection containers.

As seen in FIGS. 2, 3 and 4, a valve assembly 42 is adapted to frictionally fit tightly over the distal end 30 of drip tube 26 and control the flow of breast milk from adaptor 12 to reservoir 32. Valve assembly 42 in the illustrated embodiment, includes a sleeve 44 having a hollow portion 46 formed within the sleeve 44. An aperture 48 is disposed at a lower, portion of the sleeve. A wall 50 closes one end of hollow portion 46.

The top portion of sleeve 44 includes a hollow tube receptacle 52 having a flared upper end 54. The tube receptacle 52 has an opening 55 that is adapted to receive a hollow hose 56 that leads to a source of cyclic vacuum pressure 57 (FIG. 1) as explained more fully in issued U.S. Pat. Nos. 7,559,915 and 8,118,772. The lower end of hollow tube receptacle 52 communicates with an aperture 58 in sleeve 44, the aperture 58 communicating with hollow portion 46 of the sleeve.

Extending downward from aperture 48 in valve assembly 42 is a tubular valve mounting assembly 60 comprising a hollow interior chamber 62 communicating with aperture 48 in sleeve 44 at one end of the chamber 62, and with an opening 64 at an opposite end of mounting assembly 60. Opening 64 is circumscribed by a rim structure 65 having an outer circular surface 66.

In the illustrated embodiment, a valve mount 68 has an interior circular surface 69 constructed to frictionally and tightly fit over outer circular surface 66 of rim structure 65. A one way valve element 70 is mounted in opening 72 of mount 68 to allow breast milk to pass in one direction from the lactating woman's breast eventually into reservoir 32. The valve 70 also prevents the reverse flow of milk from the reservoir 32 into vacuum hose 56 or into drip tube 26.

The adaptor 12, valve assembly 42, hose 56, valve 70 and reservoir 32 may all be disassembled from each other for ease of cleaning. The valve assembly 42 is removed from adaptor 12 by applying manual force to overcome the friction fit that holds valve assembly 42 to adaptor 12 when in use. Hose 56 is manually removed from receptacle 52 by applying a slight upward axial force. Reservoir 32 is removed from adaptor 12 by applying manual pressure to tab 24 of the adaptor, and applying an opposite manual force to reservoir 32 to release bead 36 from groove 38. To replace one-way valve 70 after cleaning, mount 68 with valve 70 attached is reattached frictionally to outer circular surface 66.

In the illustrated embodiment, valve 70 is a duckbill check valve. Duckbill valves commonly have a duckbill-shaped inner elastomeric sleeve that responds to changes in fluid pressure, both on the internal and external surfaces of the valve. In the present invention, the valve 70 comprises two soft adjacent walls, with a slit at the bottom of the valve. The slit opens when there is positive pressure or no vacuum pressure if the valve's outer walls are not submersed in milk. When vacuum pressure is applied, the two walls are "sucked" together. As the reservoir fills with collected milk and submerses the valve, liquid pressure surrounding the valve 70, in the absence of a vacuum, also keeps the valve 70 closed. Vacuum pressure causes valve 70 to close and stops migration back into the drip tube and valve assembly from backflow milk pressure in the reservoir caused by the cyclic application of vacuum pressure during the milk pumping process, thus preventing milk from the reservoir 32 from being drawn into hollow hose 56, which prevents damage to the vacuum pumping system. When the milk pumping cycle is relieved of the vacuum pressure, or the source of vacuum pressure cycles off, valve 70 opens, as will be explained, to allow milk to advance from drip tube 26 to the interior volume 40 of reservoir 32. The buildup of milk in interior chamber 62 of valve assembly 42, combined with positive pressure returning during the pump's positive cycle, forces duckbill valve 70 open, as the pressure behind the milk passing through valve 70 is temporarily greater than the ambient pressure of the milk in the reservoir which is acting across the duckbill shaped outer surfaces of the valve, so the valve 70 opens and milk flows through the valve. However, during a vacuum portion of the pumping cycle, the vacuum pressure pulls on the inner walls of the valve, and the duckbill elastomer valve 70 flexes closed, preventing the backflow of milk out of reservoir 32. Other suitable one-way check valves may be used in place of the illustrated duckbill valve 70.

FIGS. 3 and 4 illustrate sleeve 44 of valve assembly 42 mounted via friction fit to the outer surface 74 of drip tube 26. When properly located, chamber 29 is created in the space between distal end 30 of drip tube 26 and rear wall 50 of valve assembly 42. Aperture 58 in sleeve 44 aligns with opening 76 in shroud portion 27, such that hollow tube receptacle 52 and hollow vacuum hose 56 communicate with chamber 29. In addition, in the assembled condition, aperture 28 in drip tube 26 aligns with aperture 48 in sleeve 44, such that the interior of drip tube 26 communicates with interior chamber 62 of valve mounting assembly 60, and with one-way valve 70. An aperture 80, located at the bottom of chamber 29, communicates between chamber 29, interior chamber 62 in valve assembly 42, and drip tube 26, the latter through apertures 28 and 48.

In operation, the breast milk collection device 10, as shown in FIGS. 1 and 2, is assembled as shown in FIGS. 3 and 4. Valve assembly 42 is attached over the distal end of drip tube 26, and then hollow hose 56 is inserted into flared upper end 54 of hollow tube receptacle 52. Hose 56 is manually manipulated into receptacle 52 until the hose 56 wedges itself into receptacle 52. Next, reservoir 32 is inserted into rim 20 of plate 16 until bead 36 is fully seated in groove 38.

The end of hose 56 shown in FIGS. 2 and 3 is now wedged into a frictional fit into the flared upper end 54 of receptacle 52, which holds hose 56 in engagement with receptacle 52. The hose 56 extends outward from collection device 10 through opening 22 in rim 20 of adaptor 18, which opening 22 aligns with opening 78 in reservoir 32. Tab 24 is used to grip adaptor 12 when attaching reservoir 32 to adaptor 12, and also to remove the reservoir from the adaptor.

One or a pair of milk collection devices 10 are then inserted onto the breast and into one or each of the cups of the nursing or standard brassiere of the lactating woman to be held in place there. One or both breasts will firmly fit into a respective funnel-shaped central portion 14 of each adaptor. The contact between the breast and the adaptor 12 creates a seal, whereby the negative pressure created by the vacuum force applied to the outer end of the breast does not escape between the breast and the adaptor.

The outer end of hollow hose 56 is attached to a cyclical operating vacuum pump (not shown) as is known in the art. The pump furnishes alternating vacuum pressure and relief to ambient pressure to the interior of hose 56 and to aperture 58. The cyclical vacuum pressure then passes through opening 76, and into chamber 29. The cyclical vacuum pressure then enters through aperture 80 (FIGS. 2, 3, 4) in valve mounting assembly 60, and then through aligned apertures 28 and 48 into drip tube 26. The nipple of the breast extends into the drip tube 26, as previously explained, and the cycle of applying and relieving the vacuum pressure on the breast causes milk to be expressed from the breast and into the drip tube.

At this time, the milk expressed during the previous cycle and any remnants from the previous cycle is migrating through interior chamber 62 and valve 70 to reservoir 32 where the milk is stored, and little or no milk remains in drip tube 26 or in interior chamber 62 of valve mounting assembly 42, thereby preventing the possible back flow of milk into hollow tube 56.

As the above milk-expression cycles repeat, the fluid level in internal volume 40 of reservoir 32 rises eventually to a level above the location of one-way valve 70. The then submerged valve 70 continues to function normally as the level of milk in reservoir 32 rises and submerses the valve. As the milk in reservoir 32 rises, the outer submerged walls of valve 70 are collapsed together by the vacuum pressure during the negative cycle and are also being compressed by the liquid pressure of the milk in the reservoir when the pump is turned off, thus closing the valve and preventing the backflow of milk into drip tube 26 and adaptor 12, even during the absence of vacuum pressure in hollow hose 56. This allows the maximum internal volume 40 of reservoir 32 to be utilized, thus collecting the maximum amount of expressed milk.

The foregoing description of illustrated embodiment of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed is:

1. A breast milk collection device, comprising:
   a funnel having a wide end adapted to receive a woman's breast therein and a narrow end opposite said receiving end, said narrow end forming a drip tube, said drip tube extending forwardly from said narrow end;
   a distal end of said drip tube having an aperture adjacent the distal end;
   a reservoir enclosing said funnel to form a single unit with said funnel, an internal volume of said reservoir adapted to receive breast milk through said aperture of said drip tube;
   cyclical application and relief of said vacuum pressure adapted to encourage the expression of breast milk from said breast;
   said cycle portion relieving said vacuum pressure adapted to allow the capture and collection of said breast milk in said reservoir;
   a valve assembly in communication with said aperture in said distal end of said drip tube;
   said valve assembly including a valve element extending into said reservoir, said valve element adapted to be submerged in said breast milk when the level of said milk reaches and exceeds the position of said valve element in said reservoir, said valve element closing under the force of fluid pressure exerted by the milk on the valve element;
   said valve assembly includes a sleeve removably mounted over said drip tube;
   said sleeve having a second aperture that aligns with said aperture in said drip tube when said sleeve is mounted on said drip tube; and
   said aperture in said drip tube and said second aperture in said sleeve communicating between said drip tube and said valve element.

2. The breast milk collection device of claim 1, wherein:
   said valve assembly includes a valve mounting assembly having an interior chamber extending between said aligned aperture in said drip tube and said second aperture in said sleeve, and said valve element, said interior chamber adapted to convey breast milk from said aligned apertures in said drip tube and said sleeve to said valve element.

3. The breast milk collection device of claim 1, wherein:
   said valve element opens during said cycle portion relieving vacuum pressure in said drip tube, said opening of said valve element adapted to allow milk to advance from said drip tube through said interior chamber and into said reservoir.

* * * * *